US008334370B1

(12) United States Patent
Stavrianopoulos et al.

(10) Patent No.: US 8,334,370 B1
(45) Date of Patent: *Dec. 18, 2012

(54) POLYNUCLEOTIDES COMPRISING INTERCALATING ENTITIES

(75) Inventors: Jannis Stavrianopoulos, New York, NY (US); Elazar Rabbani, New York, NY (US)

(73) Assignee: Enzo Biochem, Inc., Farmingdale, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/956,566

(22) Filed: Oct. 5, 1992

Related U.S. Application Data

(60) Division of application No. 07/394,284, filed on Aug. 15, 1989, now abandoned, which is a continuation of application No. 06/808,757, filed on Dec. 13, 1985, now abandoned.

(51) Int. Cl.
*C07H 21/00* (2006.01)
*C07H 21/02* (2006.01)
*C07H 21/04* (2006.01)
*C12Q 1/68* (2006.01)

(52) U.S. Cl. ............. 536/24.3; 536/25.32; 435/6.1; 436/172

(58) Field of Classification Search ............. 536/22.1, 536/24.3, 25.32, 23.1; 435/6, 5; 935/5, 8, 935/77, 78; 436/164, 172, 800, 805
See application file for complete search history.

(56) References Cited

U.S. PATENT DOCUMENTS

| | | | | |
|---|---|---|---|---|
| 4,486,539 A | * | 12/1984 | Ranki et al. | 436/504 |
| 4,547,569 A | * | 10/1985 | Letsinger | 536/29 |
| 4,711,955 A | * | 12/1987 | Ward | 536/29 |
| 4,835,263 A | * | 5/1989 | Nguyen | 536/27 |
| 5,593,867 A | | 1/1997 | Walker et al. | |
| 5,989,809 A | * | 11/1999 | Stavrianopoulos | 435/6 |

FOREIGN PATENT DOCUMENTS

| | | |
|---|---|---|
| EP | 0070685 | 1/1983 |
| EP | 0097373 | * 1/1984 |
| EP | 0144914 | 6/1985 |
| EP | 0 212 546 A2 | 3/1987 |
| WO | WO 8403285 | 8/1984 |

OTHER PUBLICATIONS

Asseline et al. J. BiologChem (1985) 260: 8936-8941.*
Asseline et al. Proc Natl Acad Sci, USA (1984) 81: 3297-3301.*
Asseline et al. EMBO J. 1984. 3: 795-800.*
Gaugain et al. Biochemistry. 1978. 17:5071-5078.*
Ibelgaufts, H., *Gentennoloqie von A bis Z*, p. 137-138, VCH Verlagsgesellschaft, Weinheim Germany (1980) [Translation Provided].
Stryer, L., *Biocheme 3., durchgesehene Auflage*, p. 502, Braunschweig, Weisbaden, Germany (1985) [Translation Provided].
J.W. Levinson, et al.,"Fluorescent Labeling of DNA in Solution With Covalently Bound Acriflavin", Biochemica et Biophysica Acta, 447 (1976) 260-273.
Maxam and Gilbert,"Sequencing End-Labeled DNA With Base-Specific Chemical Cleavages", Methods in Enzymology, vol. 65, 499-595, 1980.
Rigby et al.,"Labeling Deoxiribonucleic Acid to High Specific Activity in Vitro by Nick Translation With DNA Polymerase I", J. Mol. Biol. (1977) 113, 237-251.
Kriek and Emmelot,"Methylation of Deoxyribonucleic Acid by Diazomethane", Biochemica et Biophysica Acta, 91, (1964), 59-66.
Kochetkov et al.,"The Chemical Modification of Nucleic Acids I. The Preparation of Deuridylic RNA's", Biochemica et Biophysica Acta, 142, (1967), 35-46.
"The Extent and Specificity of the Degradation of Polynucleotide Chain Under the Conditions of the Preparation of Deuridylic RNA", Biochim. Biophys. Acta, 166, (1968), 755-756.
Asseline, U., et al., EMBO Journal, vol. 3, No. 4, pp. 795-800, Jan. 16, 1984.
Asseline, U., et al., Proc. Nat'l. Acad. Sci. USA, vol. 81, pp. 3297-3301, Jun. 1984.
Asseline, U., et al., Journal of Biological Chemistry, vol. 260, No. 15, pp. 8936-8941, Jul. 25, 1985.
Stryer, L., Biochemistry, $2^{nd}$ Edition, p. 573, W.H. Freeman and Company, San Francisco, USA (1981).
Frumgarts, L.A. et al., *Molekulya Biologia 19*:1394-1399 (1985)— English Translation thereof was published in Molecular Biologia USSR 19: 1142-1147 (1985).
Yamana K. et al., *Nucleic Acids Symp Ser 27*:135-136 (1992).
Muarakami A. et al., *Nucleic Acids Research 19*(15):4097-4102 (1991).
Kumke, M.U. et al., *Anal. Chem. 69*:500-506 (1997).
Bryan R.N. and Lyle, A.J., *DNA* 3(1):124 (1984).
Bayley H. and Knowles, J.R., *Methods in Enzymology* 46:69-114 (1977).
Bolton, P.N. and Kearns, D.R., Nucleic Acids Research 5(12):4891-4903 (1978).
Hardwick J.M. et al., *The Journal of Biological Chemistry* 259(17):11090-11097 (1984).
Yang C. and Soll D, Proc.Natl.Acad.Sci.(USA) 71(7):2838-2842 (1974).
Stryer L., Ann. Rev. Biochem 47:819-846 (1978).
Hayashi K. et al., *Nucleic Acids Research* 4(11):3679-3685 (1977).
Sinha R.K. et al., *Biochimica et Biophysica Acta* 474:199-209 (1977).
Norden B., Biophysical Chemistry 4:191-198 (1976).
Cheng S. and Mohr S., Biopolymers 14:663-674 (1975).
Kim SW and Kim IG, Korean J. Biochem 15:93-107 (1983).
Ruth J.L. and Bergstrom D.E., *J. Org. Chem.* 43:2870-2876 (1978).
Draper D.E., *Nucleic Acids Research* 12(2):989-1002 (1984).
Wintermeyer W. and Zzchau H.G., *FEBS Letters* 18(2):214-218 (1978).
Draper D.E. and Gold L., *Biochemistry* 19:1774-1781 (1980).
Tournon J., *Nucleic Acids Research* 2(8):1261-1273 (1975).

(Continued)

*Primary Examiner* — Carla Myers
(74) *Attorney, Agent, or Firm* — Elie H. Gendloff, Esq.

(57) ABSTRACT

Provided are nucleic acid compositions modified with intercalating aromatic compounds attached directly or indirectly through a linker arm thereto. Modifications to the nucleotides or to the oligo- or polynucleotides involve the pentosyl moieties, the abasic moieties (without a base) and the base moieties. Useful property changes are effected and can be measured or detected when such modified nucleic acids compositions have hybridized specifically to target nucleic acids.

5 Claims, 4 Drawing Sheets

OTHER PUBLICATIONS

Beardsley K and Cantor CR, *Proc. Natl. Acad. Sci. (USA)* 65(1):39-46 1970).
Bigge CF et al., *J. Carbohydrates Nucleosides Nucleotides* 8(4):295-313 (1981).
Lamola, Leemakers PA and Weissgerber A., Eds., "Energy Transfer and Organic Photochemistry," vol. XIV, pp. 17-132 (1969), Interscience, New York.
Felsenfeld and Rich, *Biochim. Biophys. Acta* 26:475-468 (1957).
Wells and Cantor, *Nucl. Acids Res.* 8(14):3229, 1980.
Talavera et al., *Appl. Spectroscopy* 51(3):401-406 (1997).
Lottspeich and Zorbas (Hrsg.) Bioanalytik, Inhaltsubersicht, Spektrum akademischer Verlag, Berlin, Heidelberg (1998).

* cited by examiner

POLYNUCLEOTIDES COMPRISING INTERCALATING ENTITIES

REFERENCE TO OTHER RELATED APPLICATIONS

This is a divisional of U.S. patent application Ser. No. 07/394,284, filed Aug. 15, 1989 (now abandoned), which is a continuation of U.S. patent application Ser. No. 06/808,757, filed Dec. 13, 1985 (also abandoned).

BACKGROUND OF THE INVENTION

The present invention relates to a method for forming a hybrid comprising a polynucleotide compound and a target polynucleotide together with preferred polynucleotide compounds and their synthesis. The polynucleotide compound can be used as a probe or as a drug.

Hybridization with A polynucleotide probe is a well known method for verifying the presence of a target polynucleotide. Hybridization is based on complementary base-pairing. When single-stranded polynucleotide probes are incubated in solution with single-stranded target polynucleotides, complementary base sequences pair to form double-stranded hybrid molecules. The double-stranded hybrid molecules can be separated from the single-stranded polynucleotide probes by chemical or physical means. See M. Grunstein and J. Wallis, *METHODS IN ENZYMOLOGY*, volume 68, R. W. U (Ed) (1979) pp. 379-469; A. R., Dunn, and J., Sambrook, *METHODS IN ENZYMOLOGY*, volume 65; part 1, (1980) pp. 468-478; Modified Nucleotides And Methods Of Preparing And Using The Same by D. C. Ward, A. A. Waldrop and P. R. Langer, European Patent Publication Number 0,063,879 published Nov. 3, 1982; DNA Probes for Infectious Disease by A. J. Berry and J. B. Peter, Diagnostic Medicine (March, 1984) pp. 1-8; and Recombinant DNA Technology: Some Applications In Clinical Microbiology by Wie-Shing Lee and James L. Bennington, Laboratory Management (April, 1985) pp. 21-26.

The probes generally comprise a polynucleotide portion and a signalling moiety portion attached to the polynucleotide. The polynucleotide portion of the probe has the ability to base-pair, i.e. hybridize to a sequence of interest or target polynucleotide. The signalling moiety portion of the probe has or produces the means by which the presence of a hybridized polynucleotide probe can be verified. the means can be, for example, fluorescence, phosphorescence, chromagen, radioactivity, or electron density.

The method of detecting a target polynucleotide utilizing a polynucleotide probe is generally carried out, for example, by first isolating a double-stranded polynucleotide comprising a target sequence therein from a sample. The double-stranded polynucleotide can be cut into smaller segments by means of restriction endonuclease digestion and the segments separated by gel electrophoresis, after which they are transferred from the gel onto a support for example, a nitrocellulose paper. Alternatively, the double-stranded polynucleotide can be fixed directly on the nitrocellulose without any prior enzyme digestion. The fixed polynucleotides are contacted with a solution containing the polynucleotide probe and the support is heated to about 80-90° C. to denature the polynucleotide double-strands. (The double-strands can also be denatured by means of alkali). The sample which now contains both the target polynucleotide and the polynucleotide probe is allowed to cool to an appropriate temperature during which time hybridization between the polynucleotide probe and the target polynucleotide takes place. After sufficient time has elapsed for hybridization to be complete, which can be for ten minutes to several hours, the fixed target polynucleotide is washed to remove all unbound polynucleotide probes. The signalling moiety portion of the polynucleotide probe is now detected, either directly, for example, by means of radioactivity or fluorescence, or indirectly, for example, by means of a chromogen formed by an enzymatic reaction.

A drawback of this method is that it requires several steps before the presence of the target polynucleotide can be verified. Namely, it requires the fixation of the target polynucleotide to a support, the contacting of the target polynucleotide with a polynucleotide probe, and the removal of all unhybridized polynucleotide probes from the support.

Recently, a method for detecting the presence of a target polynucleotide by means of a homogeneous (or one-step) nucleic acid hybridization assay was reported. The method comprises hybridizing first and second single-stranded polynucleotides, both of which contain light-sensitive labels, with a complementary single-stranded polynucleotide target from a sample such that non-radiative energy transfer occurs between the light-sensitive labels of the first and, second polynucleotides. At least one of the light-sensitive labels is of the absorber/emitter type such that energy absorbed from the other light-sensitive label is reemitted at a different wavelength. These secondary emissions can only occur if hybridization of both the first and second single-stranded polynucleotides to the target polynucleotide has taken place. The quantity of the target polynucleotides in the sample is related to the amount of secondary light emitted. See European Patent Publication No. 0,070,685 by Michael James Heller, published Jan. 26, 1983.

A drawback of this method is that it requires two separate polynucleotide probes to detect the presence of a target polynucleotide. In addition, the method requires the presence of a chemiluminescent catalyst, an absorber/emitter moiety, and chemiluminescent reagents effective for causing light emission in the presence of the chemiluminescent catalyst. Furthermore, only one label can be attached per polynucleotide probe because the light-sensitive label is attached to the sugar moiety of a terminal nucleoside. Also, the bulky labels may prevent hybridization of the complementary bases adjacent to the labels.

A method has been reported recently whereby a target polynucleotide is hybridized to a probe polynucleotide, and the resulting hybrid immobilized by its binding to an immobilized or immobilizable form of an antibody reagent selective for binding such hybrids. One embodiment is the use of an antibody selective for intercalated duplexes. This method, however, is not a homogeneous assay. In addition, the intercalating agent does not provide the signal directly upon hybridization of the probe to the target. Furthermore, the intercalating agent is attached directly to a base without a linker arm at positions required for base-pairing. See European Patent Application number 146,039 by J. P. Albarella et. al., published Jun. 26, 1985.

Fluorescent intercalating moieties attached to a polynucleotide have been reported in the literature. They are prepared by reacting the adenine or cytosine bases with a bifunctional reagent such as chloracetaldehyde to produce an aromatic tricyclic compound. See "Fluorescent Adenosine and Cytidine Derivatives" by J. R. Barrio, J. A. Secrist III, and N. J. Leonard, (1972), B.B.R.S. 46, (2), pp. 597-604, and "Physical Studies of Choloroacetaldehyde labelled fluorescent DNA" by C. H. Lee and J. G. Wetmur, (1973), B.B.R.S. 50 (3), pp. 879-85. This method has a drawback in that the bases converted to fluorescent moieties cannot base-pair, and thus such fluorescent moieties destabilize the hybridization process.

BRIEF SUMMARY OF THE INVENTION

A method for forming a hybrid comprising a target polynucleotide and a polynucleotide compound is disclosed herein together with preferred polynucleotide compounds. The polynucleotide compounds can be used for detecting the presence of a single or double-stranded target polynucleotide in a homogeneous, i.e. one-step assay, or for competitively displacing a homologous polynucleotide from a target double-stranded polynucleotide or stably binding to a target single-stranded polynucleotide to prevent transcription or replication of the target polynucleotide.

The polynucleotide compound comprises a polynucleotide and at least two entities attached to the polynucleotide by means of linker arms. The polynucleotide is able to base-pair or hybridize to a target polynucleotide. Upon the hybridization per se of the polynucleotide portion of the probe to the target polynucleotide, a change is generated in at least one property of either the polynucleotide compound, of the target polynucleotide, or of both, wherein the change constitutes the signal. If the affected property is that of the polynucleotide compound, it can be either that of the polynucleotide or that of the entity.

When the polynucleotide compound is used to detect the presence of a target polynucleotide by means of the change in a property, then the polynucleotide compound serves as a polynucleotide probe. When the polynucleotide compound is used to displace a homologous polynucleotide from a double-stranded target polynucleotide or to stably bind to a single-stranded target polynucleotide, then the polynucleotide compound serves as a polynucleotide drug.

Preferred polynucleotide compounds comprise at least one moiety having the structure wherein B represents a base selected from the group consisting of pyrimidines, purines, and deazapurines, provided that whenever B is a pyrimidine, the sugar is attached to the $N^1$ position of the pyrimidine, and whenever B is a purine or deazapurine, the sugar is attached to the $N^9$-position of the purine or deazapurine;
wherein "Phen" represents any phenanthridine moiety;
wherein said L.A. is a linker arm comprising at least three carbon atoms, and is attached to the 5-position of said phenanthridine moiety; and
wherein Z is either H or O—.

OBJECTS OF THE INVENTION

It is an object of this invention to provide a method for detecting the presence of a target polynucleotide by means of a homogeneous assay which utilizes a polynucleotide probe comprising a polynucleotide and at least two entities attached to the polynucleotide, wherein upon the hybridization per se of the polynucleotide to the target polynucleotide, a change is generated in at least one property of either the polynucleotide compound, of the target polynucleotide, or of both, wherein the change constitutes the signal.

It is another object of this invention to provide a method for preventing the transcription of a target polynucleotide by utilizing a polynucleotide compound for displacing its homologous polynucleotide from a double-stranded polynucleotide, wherein the polynucleotide compound comprises a polynucleotide and at least two entities, which entities enhance the binding of the polynucleotide portion of the polynucleotide compound with the target polynucleotide. so that its binding is greater than that of the binding of the displaced homologous polynucleotide with the target polynucleotide, thus preventing the transcription or translation of the target polynucleotide.

It is an additional object of this invention to provide a method for preventing the transcription or translation of a target polynucleotide by forming a hybrid comprising a polynucleotide compound and a target polynucleotide, wherein the polynucleotide compound comprises a polynucleotide and at least two entities attached to the polynucleotide, wherein the entities enhance the stability of the hybrid so that the polynucleotide portion of the polynucleotide probe cannot be readily displaced by another homologous polynucleotide, thus preventing the transcription or translation of the target polynucleotide.

It is a further object of this invention to provide a method for detecting the presence of a target polynucleotide by means of a homogeneous assay which utilizes a polynucleotide probe comprising a polynucleotide and at least two radiation-emitting entities attached to the polynucleotide, wherein the energy of emission of these entities is shifted upon the hybridization per se of the polynucleotide portion of the polynucleotide probe to the target polynucleotide, and wherein the shift in the energy of radiation is the signal.

It is also an object of this invention to provide a method for detecting the presence of a target polynucleotide by means of a homogeneous assay which utilizes a polynucleotide probe comprising a polynucleotide and at least two radiation-emitting entities attached to the polynucleotide, wherein the energy of emission of these entities is shifted upon intercalation of the entity into a polynucleotide hybrid, wherein these radiation-emitting entities can substantially intercalate only into a hybrid formed as a result of the hybridization of the polynucleotide portion of the polynucleotide probe to the target polynucleotide, and wherein the shift in the energy of radiation is the signal.

It is another object of this invention to provide a method for detecting the presence of a target polynucleotide by means of a homogeneous assay which utilizes a polynucleotide probe comprising a polynucleotide and at least two fluorescence-emitting entities attached to the polynucleotide, wherein the emitted energy of fluorescence of these entities is shifted upon the intercalation of these entities into a polynucleotide hybrid, wherein these fluorescence-emitting entities can substantially intercalate only into a hybrid formed as a result of the hybridization of the polynucleotide portion of the polynucleotide probe to the target polynucleotide, and wherein the shift in the emitted fluorescence energy is the signal.

It is an additional object of this invention to provide polynucleotide compounds comprising a polynucleotide and at least two fluorescent-emitting entities attached to the polynucleotide, wherein the fluorescent-emitting entities show a shift in the emission energy of fluorescence upon intercalation into a polynucleotide hybrid, and wherein the fluorescence-emitting entities can substantially intercalate only into a hybrid formed as a result of the hybridization of the polynucleotide portion of the polynucleotide compound to the target polynucleotide.

DETAILED DESCRIPTION OF THE INVENTION

A. General Description of the Polynucleotide Compound

This invention discloses the use of a polynucleotide compound. The polynucleotide compound comprises a polynucleotide portion and at least two entity portions attached to the polynucleotide. The entities should be attached to nucleotide moieties which are separated from each other by about a stretch of ten other nucleotide moieties. This is to provide target-specificity to the polynucleotide portion. The entity portion has a characteristic which upon the hybridization of the polynucleotide portion of the polynucleotide compound to a target polynucleotide, the characteristic enables the generation of a change in a property of either the polynucleotide compound or the target polynucleotide. The property change in the polynucleotide compound can be either in the polynucleotide portion or in the entity portion.

This property change can be utilized in two ways. One way is to monitor this property change in order to detect the presence of a target polynucleotide. In this instance, the polynucleotide compound is used as a polynucleotide probe. A second way is to utilize this property change to either permit the displacement from a target polynucleotide of a polynucleotide homologous to that of the polynucleotide portion of the polynucleotide compound, or else to stably bind the polynucleotide portion of the polynucleotide compound to a target polynucleotide. In this instance, the polynucleotide compound is used as a polynucleotide drug.

B. Description of the Polynucleotide Probe

1. General Description

This invention permits the polynucleotide compound to be used as a polynucleotide probe to detect the presence of a target polynucleotide in a homogeneous or one-step assay. The polynucleotide probe comprises a polynucleotide and at least two entities attached to the polynucleotide. The entity has a characteristic, such that upon the hybridization of the polynucleotide portion of the polynucleotide probe to the target polynucleotide, the characteristic enables the generation of a detectable change in a property of either the polynucleotide probe, the target polynucleotide or both. If hybridization between the polynucleotide portion of the polynucleotide probe and the target polynucleotide does not in fact occur, then the change in a property is not generated. Thus, the entities permit the detection of a target polynucleotide in one-step; an additional step of removing unbound polynucleotide probes from the sample, before verification of the presence of the target polynucleotide can be achieved, is not required.

The characteristic of the entity can be, for example, its ability to assume a certain orientation or conformation with regard to the polynucleotide probe/target polynucleotide hybrid. The property change can be one of, for example, radiation emission, interaction of molecular dispersion forces, or buoyant density. Changes in radiation emission include changes in the visible, ultraviolet, infrared, fluorescence, phosphorescence, x-ray, or γ-ray spectrum of the entity. Changes in interaction of molecular dispersion forces include changes in the melting temperature of the polynucleotide probe/target polynucleotide hybrid.

The entity can be of any length, size, or shape. It can have attached to it alkyl or aromatic fragments not necessary for imparting to it the particular characteristic. Preferably, the entity is attached to a linker arm after the nucleotide comprising the linker arm is incorporated into the polynucleotide. That is the entity is attached following formation of the desired base sequence. This is because the entity is usually a bulky molecule and may make the nucleotide a poor substrate for the polymerase enzymes. In addition, the entity may be an inhibitor of the polymerase enzymes.

2. Description of One Entity

One entity that satisfies the above-described requirements is an intercalating agent. An intercalating agent is an agent, which in the presence of double-stranded polynucleotides, can position itself between two adjacent base-pairs in the double-strands, and further interact with the base-pairs of the double-strand. The hybrids can be DNA/DNA, DNA/RNA, or RNA/RNA. The characteristic of the intercalating agent is its intercalating ability into a polynucleotide hybrid.

Generally, the intercalating agents are aromatic dyes. These intercalating aromatic dyes have a planar ring structure and have distinct fluorescence emission spectra. The fluorescence is indicative of the electron delocalization of the intercalating agent, and is affected by the inductive effect of substituent groups attached to the dye and by quenching agents.

When the aromatic dye is dissolved in an aqueous or aqueous/organic solution, it is believed that the water in the solution significantly quenches the fluorescence of the dissolved aromatic dye by raising the ground-energy-state of the aromatic dye to a level higher than when the dye is in an organic medium. If the aromatic dye intercalates into a polynucleotide hybrid, the dye becomes shielded from the water. This is because the hybrid contains a relatively hydrophobic interior (the bases) and a hydrophilic exterior (the phosphates). The water thus aggregates at the exterior of the hybrid, and not at the interior. Because the fluorescence emission of the intercalating dye is no longer quenched by the water, the ground-energy-state shifts to a lower energy level, and the result is that the fluorescence emission maximum shifts to a longer wavelength. The fluorescence intensity of the dye upon intercalation is also enhanced many-fold. This shift in fluorescence emission and intensity is thus a property change that is generated in the entity, only upon the hybridization of the polynucleotide portion of the polynucleotide probe to the target polynucleotide.

A single-stranded polynucleotide probe comprising a polynucleotide and at least one intercalating aromatic dye attached to the polynucleotide is thus capable of homogeneous or one-step detection of a target polynucleotide. Upon hybridization of the polynucleotide portion of this polynucleotide probe to the target polynucleotide to form a probe/target polynucleotide hybrid, the aromatic dye intercalates into a groove of the formed probe/target polynucleotide hybrid in between stacked base-pairs. This intercalation results in a shift in the fluorescence emission and intensity of the intercalating agent. Because this shift in fluorescence occurs only if the polynucleotide portion of the polynucleotide probe actually becomes hybridized to the target polynucleotide in a sample, the additional step of having to remove unbound polynucleotide probes from the sample is not required. Thus, with the simple expediency of measuring the fluorescence spectrum of the sample, one can determine whether hybridization has occurred, and thus detect the presence of the target polynucleotide.

Any fluorescent aromatic dye that can intercalate into a polynucleotide hybrid, and which undergoes a shift in fluorescence emission upon intercalation, is suitable with this invention. Examples of suitable aromatic dyes include, but are not limited to, phenanthridines, acridines and anthracylines. Examples of phenanthridines include, but are not limited to, ethidium, propidium, butidium, pertidium, dimidium, and phenidium.

3. Description of the Polynucleotide

The polynucleotide portion of the polynucleotide probe should comprise at least about twelve bases to impart specificity to the probe. Methods for preparing a polynucleotide that is substantially complementary to a target polynucleotide are well known in the art. The most commonly used method is that of recombinant DNA and cloning. One widely used clone is the M13 phage. Briefly, the method entails (1) cleaving the M13 RF (replicative form) DNA with one of the restriction enzymes having a unique recognition sequence in the cloning region (2) ligating the desired polynucleotide into the cleaved insertion site (3) transforming E. coli host cells (4) growing these host cells on nutrient-containing plates and selecting the colorless plaques (5) amplifying the phages from single plaques in small cultures (6) harvesting the phages from culture supernatant and removing the protein coat by treatment with phenol, and (7) precipitating the purified DNA with ethanol. Greater detail can be found in M13 CLONING AND SEQUENCING HANDBOOK Published by Amersham Corporation (1983) and in MOLECULAR CLONING by T. Maniatis, E. F. Fritsch, and J. Sambrook, published by Cold Spring Harbor Laboratory (1982).

Specific polynucleotides can also be prepared with a DNA Synthesizer Instrument such as one manufactured by Applied Biosystems, 850 Lincoln Centre Drive, Foster City, Calif. 94404, using the appropriate nucleotide precursors. According to the manufacturer, one can prepare polynucleotides of about 120-200 bases with great specificity. The synthetic schemes involve the use of phosphoramidites to link together predetermined bases. Other manufacturers of polynucleotide synthesizers include Biosearch Inc., 2980 Kerner Boulevard, San Rafael, Calif. 94901, and Beckman Instruments, 1050 Page Mill Road, Palo Alto, Calif. 94304.

A polynucleotide comprising a linker arm or entity at the terminal position can also be prepared by employing the enzyme RNA ligase and, for example, the compounds pCp or pUp in which a linker arm or entity is attached to the C or U. The polynucleotides cannot be formed by nick translation, since for this invention the polynucleotide probes must be single-stranded.

4. Polynucleotide Probe Form

The entities must permit the generation of a property change only when the polynucleotide portion of the polynucleotide probe is hybridized with the target polynucleotide. The entities must not permit the generation of a property change in a hybrid wherein one of the hybrid strands is not that of the polynucleotide target. Furthermore, the target polynucleotide to which the polynucleotide portion of the polynucleotide probe hybridizes to must be one originating from the sample. Thus the polynucleotide probe must be provided to the sample comprising the target polynucleotide only in single-stranded form. If the polynucleotide probe is provided to the sample as a double-stranded hybrid and then denatured in the sample, the entities will generate a change in a property when this polynucleotide probe hybridizes with the polynucleotide to which it was originally hybridized. This will produce a false positive result.

It is preferable that the polynucleotide probe be an integral strand. That is, a change in a property of either the entities or the polynucleotide should be generated by means of the entities upon the hybridization per se of only two strands. This permits the detection of a target polynucleotide with only one polynucleotide probe molecule. However, there may be instances where the polynucleotide probe will comprise two different polynucleotide strands. This can be, for example, where each polynucleotide strand contains different entities and the two polynucleotide strands hybridize to adjacent non-overlapping sequences on the target polynucleotide. The entities of each strand cannot cause a change in a property, but all the entities together, upon hybridization per se, can cause a change in a property. Such a situation is contemplated by this invention.

5. Description of Linker Arm

The entity is attached to a polynucleotide by means of a linker arm so that there is minimal steric interference between the entity and the polynucleotide, and so that the entity can have the necessary freedom of movement to permit it to achieve the proper orientation or conformation with regard to the polynucleotide probe/target polynucleotide hybrid. The linker arm refers to a fragment in the polynucleotide probe attaching the entity portion to the polynucleotide portion. Any atoms in this fragment not essential for the presence of the characteristic in the entity or not part of the natural nucleotide is part of the linker arm.

The linker arm and/or entity must not substantially interfere with the hybridization of the polynucleotide probe to the target polynucleotide. Therefore, the linker arm and/or entity: (a) should not prevent the base to which it is attached from pairing with its complementary base; (b) should not prevent the complexing of the complementary bases, so as to prevent the hybridization of the polynucleotide probe to the target polynucleotide; (c) should not interfere with strand elongation (unless it is at a terminal position of the polynucleotide sequence); and (d) preferably, should not change the conformation of the sugar moieties in the polynucleotide.

The linker arm is generally attached covalently to the polynucleotide. The attachment is preferably to the base moiety, although it can be to the sugar moiety, or the phosphate moiety. The base moiety can be either a purine or a pyrimidine. As mentioned hereinabove, the attachment of the linker arm to the base moiety should preferably be to a position at which the linker arm does not interfere with Watson-Crick pairing of the bases. Suitable positions are, for example, positions 5 and 6 of uracil, positions 5,6, and the exocyclic 4-amino of cytosine, positions 7 and 8 of deazapurine, position 8 of guanine, and positions 8 and the exocyclic 6-amino of adenine. Bases containing substituents at these positions are therefore not preferred for the attachment of the linker arm to those positions. A preferred linker arm for attachment to the base moiety is allylamine. See European Patent Publication No. 0,063,879 by David Ward et al., published Nov. 3, 1982 which is hereby incorporated by reference.

Preferred positions on bases are the 5 and 6 positions of pyrimidines and the 7 position on deazapurines, since 8-purine nucleotides are poor substrates for the polymerase enzymes, and the exocyclic amino group of either adenine or cytosine is involved in base-pairing to thymine and uracil, or to guanine respectively. Although a substituent at an exocyclic amino group of a base does not prevent that base from pairing to its complementary base, the substituent may alter the optimum orientation between the two bases. Preferred pyrimidines are uracil and cytosine, with 5 being the preferred position. Preferred purines are deazaadenine and deazaguanine.

There are few limitations as to the conditions that can be used for attaching a linker arm to the base moiety. Thus, any pH range, temperature range, reaction time, solvent, or buffer can be used as long as the functional groups on the base are not modified to the extent that the base is prevented from pairing to its complementary base, and as long as the base moiety is not cleaved from the sugar moiety. The optimum conditions will depend on the linker arm and the base, and can readily be determined by one skilled in the art.

The linker arm when attached to a base comprises the group of atoms attached to the base and to an entity. The linker arm can be joined to the base moiety by any number of methods, and must have a first functional group by means of which it can be attached to the base. The linker arm must also have a second functional group by means of which it can be attached to the entity. The linker arm can be joined to the base or entity by means of a carbon-carbon single bond, carbon-carbon double bond, carbon-nitrogen single bond, carbon-nitrogen double bond, carbon-carbon triple bond, carbon-oxygen single bond, carbon-sulfur single bond, or carbon-silicon single bond. Suitable functional groups include but are not limited to carboxylic esters, carboxylic acid halides, carboxylic acid thioesters, imides, imines, ketones, aldehydes, epoxides, halides, n-hydroxysuccinimide esters, imidates, anhydrides, isocyanates, isothiocyanates, and thioesters.

It is preferred that the linker arm joined to the base moiety comprise an olefinic bond at the alpha position relative to the base. The presence of such an alpha olefinic bond serves to sterically hold the linker arm away from the base and thus minimizes the interference of the linker arm and/or that of the entity with the hybridization process.

It is not necessary that the linker arm be attached to the base as one fragment. The linker arm can be constructed by attaching a first fragment to the base, followed by the attachment of a second fragment to the first fragment. Examples of suitable first fragments are:

Examples of suitable second fragments are:

N-hydroxysuccinimide esters imidates anhydrides isothiocyanates thioesters

General methods for attaching a linker arm onto a base are discussed in J. L. Ruth and D. E. Bergstrom, J. Org. Chem., 43, 2870, (1978); D. E. Bergstrom and M. K. Ogawa, J. Amer. Chem. Soc. 100, 8106, (1978); and C. F. Bigge, P. Kalaritis, J. R. Deck, and M. P. Mertes, J. Amer. Chem. Soc. 102, 2033 (1980). One preferred method is the one disclosed in detail in European Patent Application Number 0,063,379, by David C. Ward, et al., published in Nov. 3, 1982, which is hereby incorporated by reference. The method involves reacting a linker arm or a linker arm fragment containing an alpha vinyl group with a mercurated base in the presence of $K_2PdCl_4$, wherein the mercury is bound as $Hg^+$ to the position of the base which is to react with the linker arm. The scheme is shown below.

There are no particular size or content limitations for the linker arm. The linker arm can contain from about two carbons to about any number of carbons, as long as the linker arm permits the aromatic dye to intercalate into the polynucleotide probe/target polynucleotide hybrid, and does not permit the aromatic dye to intercalate into other strands. The linker arm can contain heteroatoms and unsaturations. The linker arm can comprise aliphatic, alicyclic or aromatic moieties. The actual size or content of the linker arm will depend on the entity chosen, and the method by which the entity generates a change in a property upon the hybridization per se of the polynucleotide portion of the polynucleotide probe to the target polynucleotide.

Attachment of the linker arm to the sugar moiety of the polynucleotide sequence can be my means of a Schiff base to the 1' aldehyde following depurination or depyrimidation of preselected bases, or it can be to the 2' hydroxy in the case when the sugar is ribose. The linker arm when attached to the 1' aldehyde can comprise, for example, an amine, hydrazine, or hydrazide functionality. Such a method is disclosed in pending patent application Ser. No. 06/765,288 by Jannis Stavrianopoulos, filed on Aug. 13, 1985, and assigned to the same assignee which is hereby incorporated by reference. Attachment of a linker arm to the phosphate moiety can be by alkylation of the phosphate moiety. See U.S. Pat. No. 4,469,863 by P. O. P. Ts'O and P. S. Miller which is hereby incorporated by reference.

When the linker arm is attached to the base moiety, it is preferable to attach it to the base at the nucleoside or nucleotide level. This is because the reaction conditions that may be required to attach the linker arm to the base may cause undesirable side reactions to a polynucleotide. Furthermore, attachment at the polynucleotide level may give inconsistent and irreproducible yields. Attachment at the nucleoside or nucleotide level permits the modified nucleoside or nucleotide to first be purified, and then to be incorporated into a polynucleotide. The incorporation can be either by cloning, for example, in an M13 vector, or by synthesis with a polynucleotide synthesizer instrument as disclosed hereinabove.

In addition, it is preferable that the modified nucleotide be a relatively efficient substrate for the commonly studied nucleic acid polymerases, since a most efficient way of incorporating the modified nucleotide into a polynucleotide is by means of nucleic acid polymerases. Thus, the linker arm should not sterically interfere either with the active site on the enzyme or with the complementary base-pairing of the modified nucleotide. Substitution at positions that alter normal "anti" nucleoside conformation should also be avoided since such conformational changes usually render the modified nucleotide a poor substrate for the polymerase enzymes.

When the linker arm is attached to the 1' aldehyde of the sugar, the linker arm must be attached following the formation of the polynucleotide portion of the polynucleotide probe. This is because attachment of the sugar requires a free aldehyde at the 1-position of the sugar. The free aldehyde is formed by depurination or depyrimidation. A moiety comprising a sugar and phosphate without a base is not a substrate for the polymerase enzymes. Thus, the linker arm must be attached by first selectively depurinating or depyrimidating the desired polynucleotide sequence, and then attaching the linker arm, to the sugar by means of the aldehyde. When the linker arm is attached to the 2' hydroxy of a ribose sugar, the linker arm can be attached at the nucleotide or polynucleotide level. This is because modified nucleotides can, be incorporated into a polynucleotide by means of a gene-synthesizer instrument. When the linker arm is attached to the phosphate, the linker arm must be attached at the nucleoside or nucleotide level so that the attachment is not at positions other than the phosphate.

6. Attachment of the Entity

The entity can be attached covalently to the linker arm, for example, by means of any of the functional groups described above. An example, would be the reaction of an amino, thio, or oxo group on the entity with another functional group on the linker arm, such as an isothiocyanate, an epoxide, a carbodiimide, a carboxylic acid anhydride, a carboxylic acid ester, a carboxylic acid chloride, a carboxylic acid, a thioester, an imine, a halogen, a ketone, or an aldehyde.

The entity can also be attached to the linker arm non-covalently, for example, by means of a chelator attached to the linker arm and also to the entity. A coordination metal can sandwich the entity and the linker arm to form a complex. Preferred chelators include, but are not limited to, ethylenediaminetetraacetic acid (EDTA), diethylenetriaminepentaacetic acid (DTPA) and trans-diaminocylcohexanetetraacetic acid (DCTA); preferred metals comprise the various transition metals, particularly those of the lanthanide metals.

Although the attachment of an aromatic dye non-covalently to a linker arm is not as stable or as strong as covalent attachment, since this assay is carried out in one-step which does not involve many manipulations following the addition of the polynucleotide probe to the sample containing the target polynucleotide, the electrostatic attraction may provide sufficient bond strength to permit the generation of a change in a property. This can be the case when the entity is an aromatic dye agent and only the intercalating step is required for a change in a property. Here the intercalation of the aromatic dye into the formed polynucleotide probe/target hybrid can generate a shift in fluorescene emission so that the presence of the target polynucleotide can be verified.

Varying conditions can be used for attaching an intercalating aromatic dye entity to a linker arm. Generally, any pH range from about 4 to about 10, preferably from about 5 to about 8, any temperature from about 20° C. to about 100° C., preferably from about 40° C. to about 65° C., any solvent, and any buffer or catalyst can be used as long as the pH, temperature, solvent, or buffer does not modify any of the group or moieties of the polynucleotide. Thus, for example, reagents or conditions that can depurinate or deaminate the polynucleotide should be avoided. There are also relatively few limitations as to reaction times. The optimum pH, temperature, solvent, or reaction time for attaching an aromatic dye to a linker arm will depend on the linker arm, the aromatic dye, and the functionalities to be reacted. The conditions can readily be determined by one skilled in the art.

Most intercalating aromatic fluorescent dyes are not soluble in water and thus attachment of the aromatic dye to the linker arm of the polynucleotide will require a mixed miscible solvent system, such as a mixture of water with either ethanol, methanol, tetrahydrofuran, dioxane, propanol, selected ethers, esters, ketones, amids, glycerin, acetone, pyridine, dimethylformamide, dimethylsulfoxide, and hexamethylphosphoramide. Alternatively, a two phase immiscible solvent system could be used in which the aromatic dye is dissolved in an organic solvent and the polynucleotide is dissolved in an aqueous solvent. In this instance, the two solvent systems will have to be constantly mixed to contact the polynucleotide with the aromatic dye so that they can react. Following their reaction, the polynucleotide probe will generally be in the aqueous solution while the aromatic dye will remain in the organic solution.

The stoichiometry of the reactants required for these reactions can vary widely. Generally, an excess of the component that is more easily prepared will be used for the attachment of the aromatic dye to the polynucleotide. In practice, the amounts will vary depending upon the required reaction conditions, the aromatic dye, the linker arm, and their reacting functional groups.

The intercalating aromatic dye generally will have to be attached to the linker arm after incorporation of the nucleotide containing the linker arm into the polynucleotide. This is because most intercalating aromatic dyes inhibit polynucleotide synthesis, and thus would prevent the incorporation of a nucleotide to which an aromatic intercalating agent is attached into a polynucleotide.

7. Number of Entities

The polynucleotide probe can comprise two entities or more than two entities. The entities can be attached at terminal positions or at non-terminal positions of the polynucleotide probe. The entities should be attached to nucleotides that are separated from each other by about a stretch of ten other nucleotides to as to provide specificity to the probe. The greater the number of entities, the more sensitive the polynucleotide probe will be. However, the entities should not be present in such numbers that effective hybridization of the polynucleotide portion of the polynucleotide probe to the target polynucleotide is substantially prevented. The number of entities that can be attached will depend on which moiety the entity is attached to and the length of the polynucleotide.

Entities that are attached to a particular base moiety are limited to an amount no more than the number of that base moiety present in the polynucleotide probe. Entities that are attached to a sugar moiety are limited to an amount which doesn't prevent hybridization of the polynucleotide probe to the target polynucleotide, because in this instance each entity decreases the number of bases on the probe polynucleotide available for base-pairing. Entities that attached to a phosphate moiety are limited to an amount which does not distort the conformation of the sugar and base moieties. It is preferable that no more than one entity per four nucleotides be attached to the polynucleotide probe.

When the entity is an intercalating agent, the linker arm must be of sufficient length and have sufficient flexibility to provide freedom of movement to the intercalating agent, so that it can fold inward and become intercalated into the formed polynucleotide probe/target polynucleotide hybrid. It is understood that a linker arm that may be suitable for attachment to one position of a base may not be suitable for attachment to another position on the same base or to any position on another base, or for attachment to a position on the sugar or phosphate. For example, because the preferred conformation of a nucleotide is the "anti" conformation, an entity attached to a phosphate group, for example, would require a longer linker arm then one attached, for example, to the 5-position of a uridine. Similarly, a linker arm attached to a purine which comprises two rings may require a longer linker arm than one attached to a pyrimidine which comprises only one ring.

8. Detection of Property Changes of Intercalating Agents

Intercalating agents which are aromatic dyes generally can be detected by a shift in their fluorescence emission as described hereinabove in the section "Description of one entity". It is not, however, necessary to utilize the fluorescence property of intercalating agents, because intercalating agents, upon the hybridization of the polynucleotide portion of the polynucleotide probe with a target polynucleotide, cause a change in the $T_M$ or melting temperature of the double-strand or duplex. The melting temperature refers to the temperature at which a polynucleotide double-strand becomes denatured. Denaturation requires the breaking of the hydrogen bonds between paired-bases, and the denaturation temperature is dependent on the base-content of the strands, because G-C bonds are stronger that A-T bonds.

The presence of an intercalating agent in a double-strand strengthens the interaction between the individual strands so that the temperature required to denature the strands is considerable higher. The extent to which the melting temperature is increased will depend on the particular intercalating agents and their quantity. For example, it was found experimentally that a polynucleotide hybrid of poly A.poly T comprising one phenanthridine intercalating agent per ten base-pairs increased the melting temperature of the hybrid by about 25° C.

It is thus possible to use a polynucleotide probe whose entity is a non-fluorescing intercalating agent. One can mix the sample comprising the target polynucleotide with the polynucleotide probe, and following sufficient reaction time, precipitate the polynucleotides. One can then dissolve the precipitate in a solution, heat the solution, and monitor the temperature at which an increase in the uv absorbance (hyperchromicity) results. That temperature is indicative of the $T_M$. If upon heating the sample, one obtains two $T_M$ profiles wherein one profile is at the usual $T_M$ and the second profile is at a higher $T_M$, then the presence of the target polynucleotide is verified.

The changes in the property are generally detected by means of a device, although in some instances eye-detection is possible. Examples of devices are mineral light lamps and fluorometers. Some property changes can be detected with a device after the addition of the polynucleotide probe to the sample comprising the target polynucleotide, without undue additional experimentation. Other property changes may only be detectable upon further experimental manipulations after the addition of the polynucleotide probe to the sample comprising the target polynucleotide. Regardless, however, of whether further experimental manipulations are required or not, there is no need to separate unbound polynucleotide probes from the sample prior to verifying the presence of the target polynucleotide.

One example of the former is where the entity, for example, an intercalating agent, upon hybridization of the polynucleotide portion of the polynucleotide probe to the target polynucleotide in a solution, undergoes a shift in its fluorescence emission spectrum. In this instance, experimental manipulations are not required after the addition of the polynucleotide probe to the sample comprising the target polynucleotide. The fluorescence of the solution can be measured in a fluorometer and a change in fluorescence emission is indicative of the presence of the target polynucleotide. Another example is where the entity, for example, an intercalating agent, upon hybridization of the polynucleotide portion of the polynucleotide probe to the target polynucleotide in a solution, generates a change in the melting temperature of the polynucleotide hybrid. One need only measure the UV absorbance of the solution in a UV spectrophotometer containing a heating element, and determine the temperature at which a hyperchromic shift occurs. Because in each case it is a change in a property which is measured, a high initial background will not substantially interfere with the detection process.

An example of the latter is where the entity, for example, an intercalating agent, upon hybridization of the polynucleotide portion of the polynucleotide probe to the target polynucleotide in a solution, generates a change in the buoyant density of the polynucleotide hybrid by changing the polynucleotide tertiary structure. In this instance, further experimental manipulation is required because the solution must first be centrifuged, for example, in cesium chloride, before the density and uv measurements of the solution can be carried out.

The property change that is generated can be in the polynucleotide probe or in the target polynucleotide. When the property change is generated in the polynucleotide probe, the change can be in the entity portion of the polynucleotide probe or in the polynucleotide portion of the polynucleotide probe. An example where the change is generated in the polynucleotide probe is where a fluorescent intercalating agent is attached to a nucleotide which is not at a terminal position of the polynucleotide probe. The intercalating agent intercalates into a hybrid formed from the hybridization of the target polynucleotide with the polynucleotide portion of the polynucleotide probe. In this instance, the property changed is the fluorescence emission of the entity portion of the polynucleotide probe.

An example where the change is generated in the target polynucleotide is where a non-fluorescent intercalating agent is attached to a terminal nucleotide. The intercalating agent is attached to a linker arm by means of which it can intercalate into an adjacent hybrid, namely one comprising the target polynucleotide and an adjacent complementary polynucleotide which polynucleotide is not that of the polynucleotide probe. Here, the intercalating agent increases the $T_M$ of a hybrid but it does not increase the $T_M$ of the hybrid comprising the probe and target. However, it is the hybridization of the polynucleotide portion of the polynucleotide probe to the target polynucleotide, that enables the intercalating agent to intercalate into an adjacent hybrid, and thus to increase the $T_M$ of the adjacent hybrid. Therefore, an increase in $T_M$ verifies the presence of the hybrid. In this instance, the property changed is the thermodynamic interaction between the target polynucleotide, and the adjacent complementary polynucleotide.

Method for Detecting Target Polynucleotide

The method of this invention using a polynucleotide probe wherein a fluorescent aromatic dye is the entity can be carried out, for example, by lysing the sample comprising the target polynucleotide in a solution to release the target polynucleotide in a solution to release the target polynucleotide from the surrounding membrane. Lysis can be, for example, by exposing the sample to sonication, or to a detergent. The polynucleotides can be separated from cell debris by centrifugation, and purified further by alcohol precipitation, or by dialysis. The polynucleotide probe is then added to a solution, containing the target polynucleotide, and the solution allowed to incubate from about 10 minutes to about 24 hours at a temperature from about 20° C. to about 100° C. It is realized that the higher the temperatures, the less the time required for hybridization. The solution is then placed in a fluorometer, and the fluorescence emission is measured. A shift in the fluorescence emission spectrum of the aromatic dye from the spectrum obtained when the aromatic dye is not intercalated, indicates the presence of the target polynucleotide in the sample.

Generally, the target polynucleotide must be rendered in single-stranded form during the hybridization step before it can hybridize with the polynucleotide portion of the polynucleotide probe. This can be either by heat or alkali. However, when the entity of the polynucleotide probe is an intercalating agent, the target polynucleotide can be present either in single-stranded or double-stranded form. When the target polynucleotide is in double-stranded form, the polynucleotide portion of the polynucleotide probe displaces its homologous strand from the target polynucleotide to form the polynucleotide probe/target polynucleotide hybrid.

It is believed that the reason why this particular polynucleotide probe can be used without first denaturing the double-strand comprising the target polynucleotide is that the intercalating agents provide enhanced stability to a double-strand wherein one of the strands comprises the intercalating agents. By way of explanation, assume that a double-strand comprises strands "A" and "B", wherein strand "A" comprises the target polynucleotide. Assume also, that a polynucleotide probe is comprised of a polynucleotide portion, strand "C", which is complementary to the target polynucleotide in strand "A", and two intercalating agent entities. Assume further, that strand "D" is complementary to the target polynucleotide in strand "A".

It is known that polynucleotide double-strands or hybrids partially open-up or breathe at intervals. However, strand "D" will generally not be able to displace strand "B" at temperatures lower than the $T_M$ of the double-strand. This is because the thermodynamic interaction between strands "A" and "D" is not greater than the thermodynamic interaction between strands "A" and "B". Even if during a breathing period, wherein strands "A" and "B" should partially separate and strand "D" should start to base-pair to strand "A", this base-pairing will be of only short duration. Strand "B" which is for the most part hybridized to strand "A" will quickly displace strand "D". Strand "D" will not be able to unzipper strand "B" from strand "A" to form a double-strand comprising strands "A" and "D".

However, assume a base in strand "C" to which an intercalating agent is attached pairs to its complementary base in strand "A" during a breathing period. When this occurs, the intercalating agent attached to the base will intercalate into adjacent base-pairs. The base in strand "C" to which the other intercalating agent is attached can then also pair to its complementary base and the intercalating agent attached to that base will also intercalate into adjacent base-pairs. The result is that the two bases of the polynucleotide portion of the polynucleotide probe are paired to bases of the target polynucleotide with enhanced stability. The remaining bases in between these bases then pair to their complementary bases. The intercalating agents of strand "C" will provide a greater thermodynamic stability between the bases of strand "C" which are paired to the bases of strand "A", as compared to the bases of strand "B" which are paired to the bases of strand "A". For example, ethidium bromide increases the melting temperature of polynucleotide double-strands by about 25° C. See U. B. Le Pecq and C. Paoletti, J. M. B., (1967) 27, pp. 87-106). Strand "B" can no longer displace strand "C" from strand "A". The net result will be that a portion of strand "B" that had been previously hybridized to strand "A", will be permanently unzippered from strand "A" leaving instead a double-strand portion comprising strands "A" and "C". Thus this single-stranded polynucleotide probe will permit the detection in a sample of a target polynucleotide even if the target polynucleotide is not present in single-stranded form.

The method can also be used to detect the presence of a target polynucleotide at temperatures at which double-strands become denatured. Generally, the detection of a target polynucleotide that is present in double-stranded form is carried out by heating the sample comprising the double-strands to a temperature higher than the $T_M$ of the double-strands in the presence of the polynucleotide probe, and cooling the sample to permit the renaturation of the polynucleotide probe with the target polynucleotide. ever, when the polynucleotide probe comprises fluorescent intercalating agent entities, the sample need not be cooled. This is because the intercalating agents stabilize the base-pairs and comprises the $T_M$ of those base-pairs. Thus, when the polynucleotide portion of the polynucleotide probe commences to hybridize with the target polynucleotide, and the intercalating agents intercalate into the formed double-strand, the elevated temperature of the sample is no longer sufficient to denature this double-strand, and the presence of the target polynucleotide can be verified by the change in the fluorescence emission of the intercalating agents. It is understood that the elevated temperature cannot be higher than the $T_M$ of this double-strand, i.e. one comprising the polynucleotide probe and the target polynucleotide.

10. Target Polynucleotides

This method can be used to detect a target polynucleotide, for example, from a microorganism, a plant cell, or a mammalian cell. The microorganism can be a bacteria, fungus, virus, or yeast. The target polynucleotide can be one that is unique for a particular pathogenic virus, one that is present in a mutated mammalian gene that results in the production of a non-functioning protein, or one that imparts antibiotic resistance to a bacteria. For example, it can be one that imparts penicillin resistance in *Streptococcus pyogenes* or *Neisseria meningitidis*; tetracycline resistance in *Staphylococcus aureus, Candida albicans, Pseudomonas aeruginosa, Streptococcus pyogenes*, or *Neisseria gonorrheae*; and aminoglycoside resistance in *Mycobacterium tuberculosis*.

This approach can be extended to the diagnosis of genetic disorders, such as thalassemia and sickle cell anemia. The polynucleotide gene whose presence or absence (in the case of thalassemia) is associated with the disorder can be detected following hybridization with a polynucleotide probe according to this invention.

The mapping of genes or their transcripts to specific loci on chromosomes has been a tedious and time-consuming occupation, involving mainly techniques of cell-fusion and somatic cell genetics. Although in-situ hybridization has been employed successfully for mapping single-copy gene sequences in species that undergo chromosome polytenization, such as that of *Drosophila*, detection of unique sequence genes in most higher eukaryotic chromosomes has been extremely difficult, if not impossible, using standard hybridization methods. The necessity for polynucleotide probes of very high specific radioactivity to facilitate autoradiographic localization of the hybridization site also results in rapid radiodecomposition of the polynucleotide probe and a concomitant increase in the background noise of silver grain deposition. The use of hybridization probes with low to moderate specific radioactivities requires exposure times of many days or weeks, even to detect multicopy sequences, such as ribosomal RNA genes or satellite DNA. Since recombinant DNA technology has made feasible the molecular cloning of virtually every single-copy sequence found in eukaryotic cells, it would be extremely beneficial to have a rapid and sensitive method for mapping the chromosomal origin of such cloned genomic fragments.

Finally tumor cells can be diagnosed by preparing a polynucleotide probe according to this invention which is complementary to the messenger ribonucleic acid transcribed from a deoxyribonucleic acid gene sequence associated with the production of polypeptides, such as fetal protein antigen or carcinoembryonic antigen, the presence of which is diagnostic for specific tumor cells. Hybridization and detection of the probe/target polynucleotide hybrid would provide a method for detecting the tumor cells.

A polynucleotide probe comprising a polynucleotide and an intercalating aromatic agent attached to the polynucleotide suitable for this invention is shown below, wherein the polynucleotide comprises at least one moiety having the structure wherein B represents a base selected from the group consisting of pyrimidines, purines and deazapurines, provided that whenever B is a pyrimidine, the sugar is attached to the N'-position of the pyrimidine, and
whenever B is a purine or deazapurine, the sugar is attached to the $N^9$-position of the purine or deazapurine;
wherein "Phen" represents any phenanthridine moiety;
wherein said L.A. is a linker arm comprising at least three carbon atoms, and is attached to the 5-position of said phenanthridine moiety; and
wherein Z is either H or O—.

Generally, B will vary within the same oligo- or polynucleotide, being alternatively uracil, cytosine, thymine, guanine, adenine, deazaaguanine, or deazadenine. Also, in general, the variation will correspond to the ordered sequence of the nucleotides comprising the target polynucleotide. It is intended that the structure shown also embrace polynucleotides such as poly C, poly U, poly r(A-U), and poly d(A-U).

11. Synthesis of a Polynucleotide Probe

Figure 1:
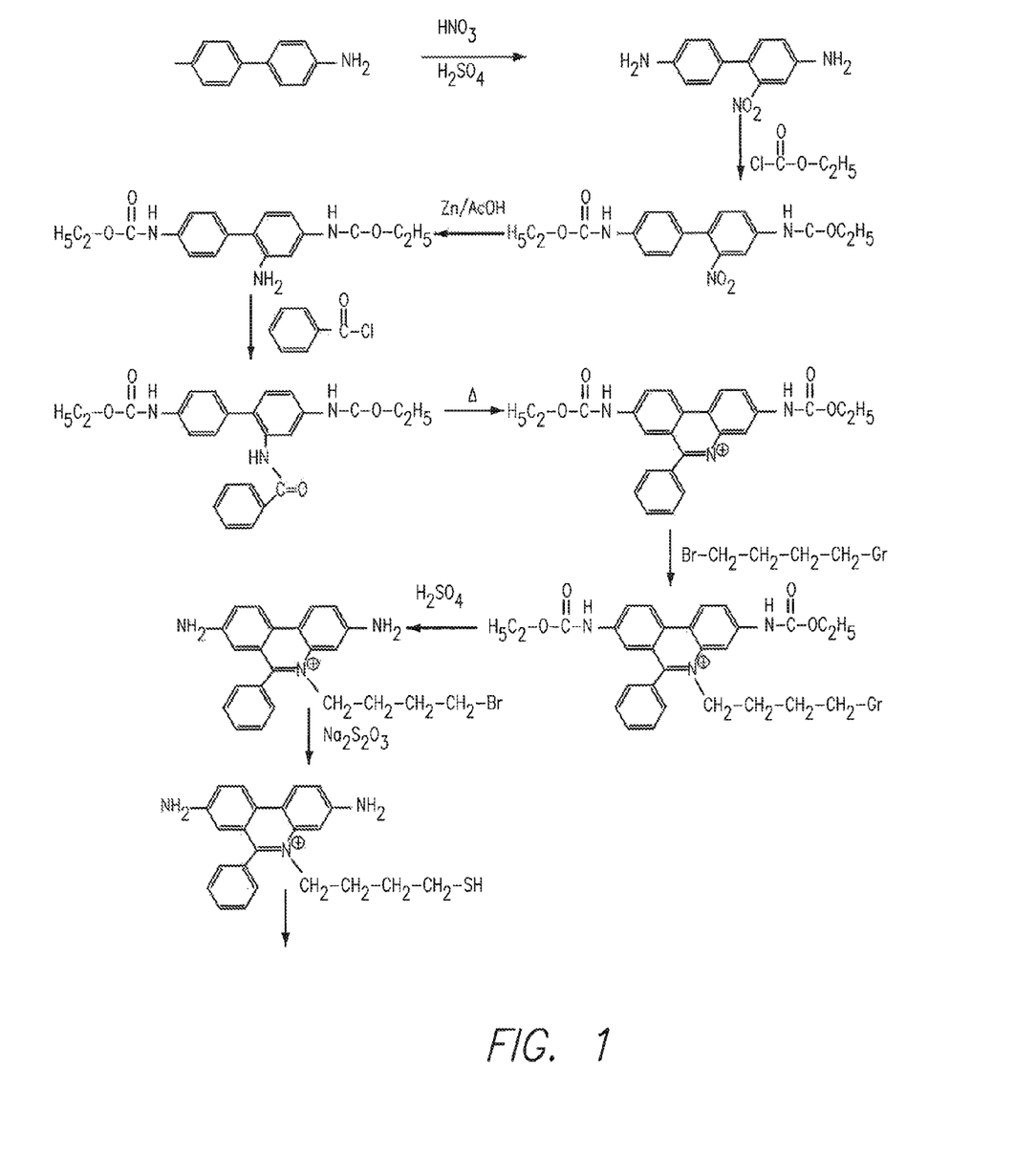
FIG. 1 depicts the synthesis of an aromatic dye that can be attached to a polynucleotide to form a polynucleotide compound.

An example of the synthesis of such a polynucleotide probe is described hereinbelow in conjunction with FIG. 1. The polynucleotide probe comprises the nucleotides dTMP and dUMP, and a butidium intercalating agent. The target polynucleotide comprises poly dAMP.

The first step of the synthesis was the nitration of benzidine to 3-nitrobenzidine with potassium nitrate in the presence of sulfuric acid. The two exocyclic amino groups were then reacted with ethylchloroformate to form the diisocyanate compound. This step was necessary because otherwise the primary amino groups would covalently react with other reagents later on to form amides, or secondary and tertiary amines. Such a reaction would prevent the synthesized entity from intercalating into a hybrid and thus would destroy its effectiveness as an entity. This fact is based on a report that while the blocking of the 8-amino group only of phenanthridium compounds with an acetyl group lowers the polynucleotide helix unwinding angle without causing a significant change in its binding energy, complete blockage of the 3- and 8-amino groups results in a greatly lower unwinding angle with a 10-20 fold reduction in the binding constant of the phenanthridium compounds. The two amino groups contribute about 1.4-1.7 cal/mole of free energy to the stability of the intercalated complex. See the Review article entitled "Ethidium and Propidium" in *Antibiotics*, vol. 3, J. W. Cozcozan and F. E. Hahn, Eds. Published by Springer-Verlag, N.Y., (1975), pp. 141-165.

The 3-nitro group was then reduced to an amino group with zinc, and benzoyl chloride was added to form the benzoyl amide. The carbonyl of this benzoyl amide upon heating in phosphoroxychloride reacted with the 6-position carbon to form the phenanthridium derivative. The 5-tertiary amine was then quarternized by reacting it with 1,4-dibromobutane to form the butidium derivative. This was followed by hydrolysis of the diurethane moieties to generate 5-(4'-bromobutyl)-3,8-diamino-6-phenylphenanthyridine. The bromine was then replaced with a thiol by reacting the compound with sodium thiosulfate to form 5-(4'-thiobutyl)-3,8 diamino-6-phenylphenanthridine. This product represented the entity portion of the polynucleotide probe and exhibited the fluorescence characteristic of butidium derivatives.

Figure 2A:
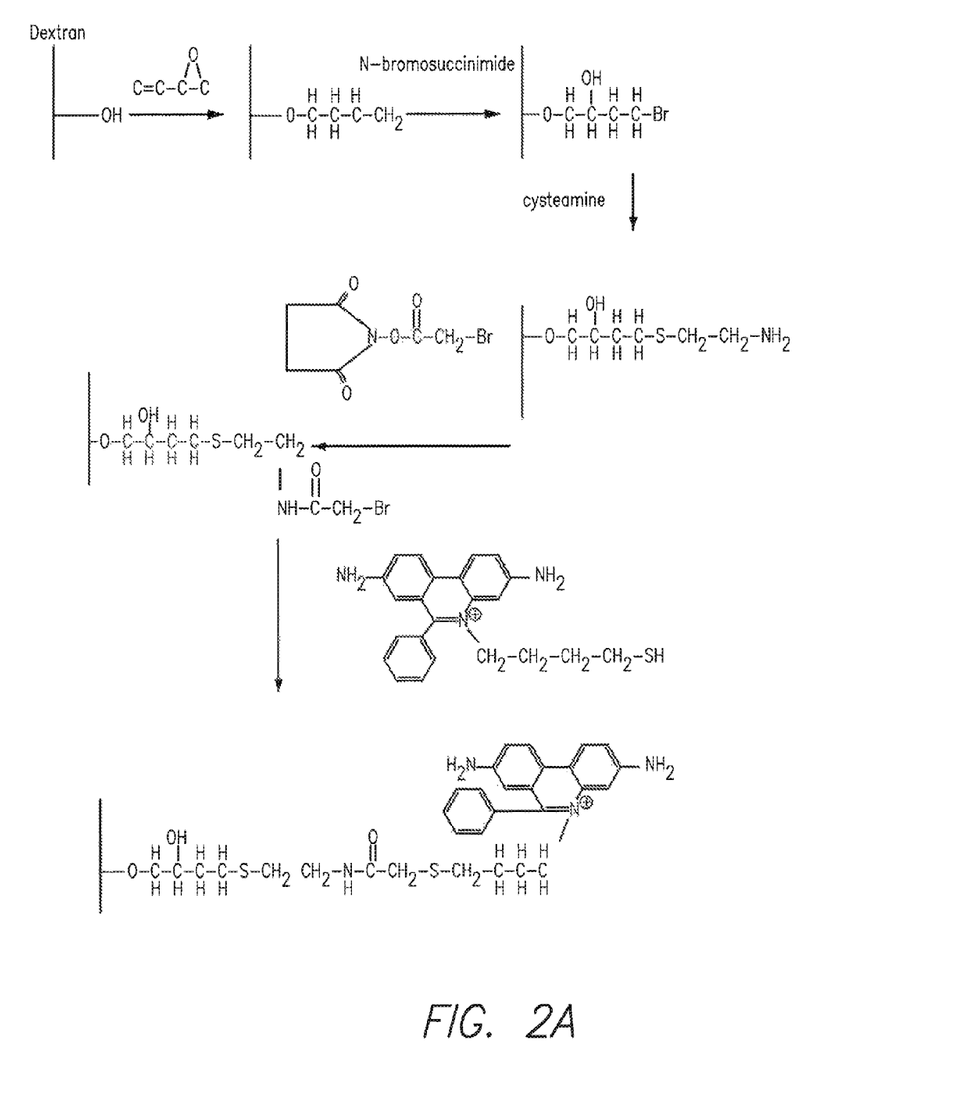
FIG. 2 shows the attachment of the aromatic dye of FIG. 1 to (a) a dextran, and (b) a polynucleotide.

Prior to attaching this compound to a polynucleotide, it was necessary to verify that the fluorescence of this compound would not be destroyed upon covalent attachment to another molecule. This was carried out by reacting the butidium compound with a bromoacetylated aminodextran derivative as shown in FIG. 2 (*a*). The dextran derivative was prepared by reacting dextran with butadiene monoepoxide in the presence of sodium borohydride to form 1-butene-4-dextran. This compound was mixed with N-bromosuccinimide to yield 1-bromobutane-4-dextran, and then further reacted with cysteamine to give an aminodextran derivative. This dextran was mixed with the N-hydroxysuccinimide ester of bromoacetic acid to form the bromoacetylated aminodextran derivative.

This bromoacetylated aminodextran derivative was reacted with the 5-(4'-thiobutyl)3,8-diamino-6-phenylphenanthridine described above to form a dextran-labeled phenanthridium compound. Spectral analysis of the product showed that the fluorescence of the phenanthridine was not altered by its attachment to the dextran.

A polynucleotide was then prepared comprising poly (dT). poly.(dU) wherein an allylamine was attached to each uracil (U) base at the 5-position. The method used to prepare the polynucleotide was to synthesize the polynucleotide with the enzyme terminal transferase in the presence of a mixture of dUTP and AAUTP (allylamine UTP). The synthesized polynucleotide was purified by anion exchange chromatography. The uracil base has an absorption maximum at about 260 nm while the uracil base containing an allylamine at the 5-position has an absorption maximum at about 290 nm. The ratio of the two bases in polynucleotide polymer can thus be determined by measuring the absorbance ratio of 260/290. It was found for this experiment that the ratio of AAdU to dU was 1:10.

Figure 2B:
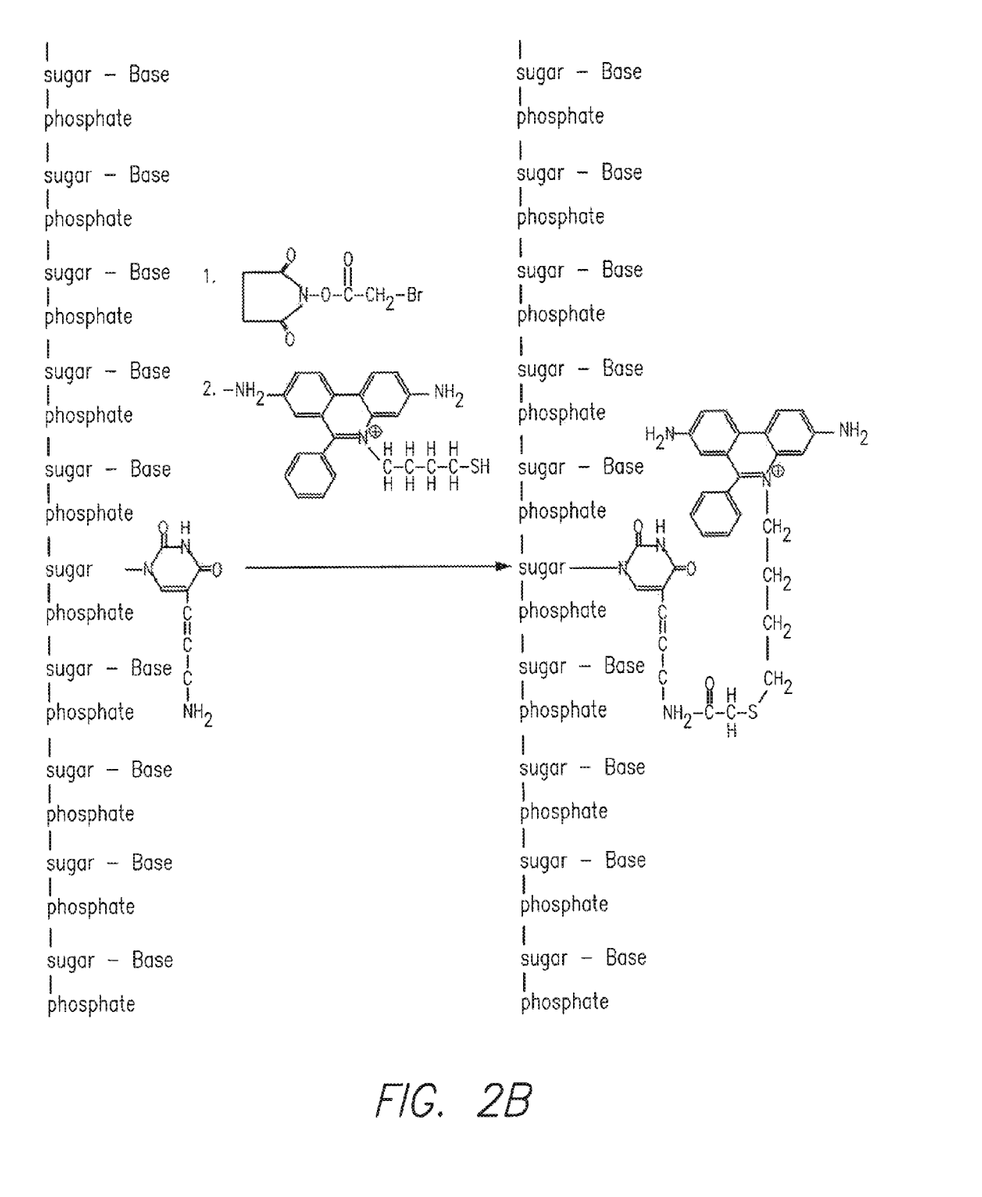
Figure 3:
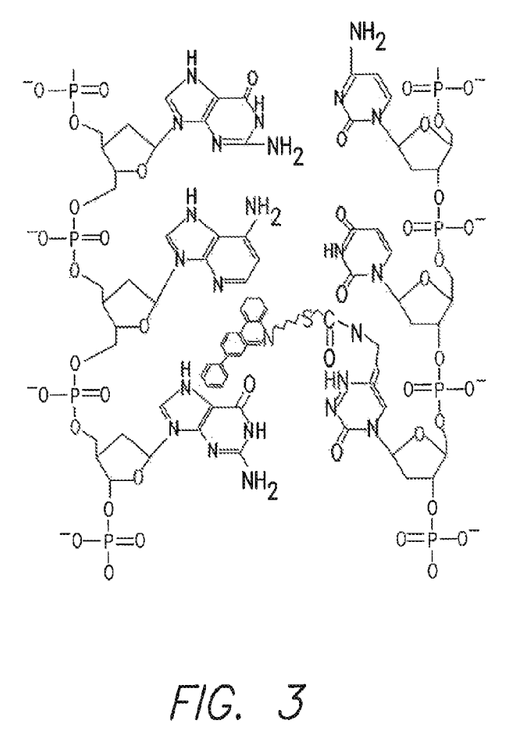
FIG. 3 shows the intercalation of an aromatic dye attached to a polynucleotide into a hybrid formed from the hybridization of the polynucleotide with a target polynucleotide.

This polynucleotide was then reacted with the 5-(4'-thiobutyl)-3,8-diamino-6-phenylphenanthridine under slightly alkaline conditions in a solution containing a mixture of water-dimethylformamide as shown in FIG. 26). The unreacted butidium derivative was extracted from the solution with butanol. Extraction with the butanol caused the polynucleotide probe to precipitate out of solution. The precipitate was further purified on an anion exchange column.

The purified polynucleotide probe was then mixed with three solutions. The first solution contained poly(rA), the second solution contained calf thymus double-stranded DNA, and the third solution contained poly(dT). Only the solution containing poly(rA) showed intense fluorescence. This showed that the intercalating agent was not intercalating into a double-strand, wherein neither strand was that of the polynucleotide probe.

The purified polynucleotide probe was mixed with a solution containing poly(dT)-poly(rA) wherein the ratio of poly (dT) to poly(rA) was 2:1. The solution fluoresced almost immediately. This verified the fact that a polynucleotide probe comprising an intercalating agent can displace an homologous polynucleotide from a double-strand.

Description of the Polynucleotide Drug

This invention permits the polynucleotide composition to be used as a polynucleotide drug. The polynucleotide drug is used to prevent the transcription or translation of a target polynucleotide. When the drug is used to prevent transcription, the target polynucleotide can be DNA or RNA. When the polynucleotide drug is used to prevent translation, the target polynucleotide is messenger RNA.

The polynucleotide drug comprises a polynucleotide and at least two entities attached to the polynucleotide. The entities have a characteristic such that when the polynucleotide portion of the polynucleotide drug is hybridized to the target polynucleotide, a change is generated in a property of either the polynucleotide probe, the target polynucleotide, or both. The property changed is the thermodynamic stability of the formed hybrid. This stability prevents the displacement of the polynucleotide drug from the target polynucleotide by a polynucleotide homologous to that of the polynucleotide of the drug, because a hybrid comprising such a homologous polynucleotide and the target polynucleotide would not be as thermodynamically stable as one comprising the polynucleotide of the drug and the target polynucleotide.

An example of a suitable polynucleotide drug is one comprising an intercalating agent as the entity. As stated hereinabove, the presence of an intercalating agent increases the $T_M$ of a polynucleotide double-strand. Thus, if a polynucleotide drug comprising an intercalating agent is mixed with a sample or administered to an organism comprising the target polynucleotide, the polynucleotide drug "seeks out" its target polynucleotide. When it finds that target polynucleotide, even though the target is already hybridized to a complementary polynucleotide, the polynucleotide portion of the polynucleotide drug will replace the sequence complementary to the target by reasons stated earlier hereinabove in the discussion of the polynucleotide probe. The effect will be to form a double-strand which will not readily become a template for polymerase and transferase enzymes, and thus shut off transcription or translation of the target polynucleotide.

This polynucleotide drug has a limitation in that the intercalating agent must be attached to the polynucleotide by means of a linker arm which permits the intercalating agent to intercalate only into a double-strand formed as a result of the hybridization of the polynucleotide portion of the drug with the target polynucleotide. The intercalating agent must not intercalate into other double-strands, so that it inhibits the transcription of translation of other polynucleotides.

This polynucleotide drug has an advantage. Most chemotherapeutic drugs, including intercalating agents when administered systemically to a human, become distributed uniformly throughout the body. Most of these drugs are very toxic. Thus, in addition to exerting a therapeutic effect at target sites, they exert toxic effects at non-target sites. Intercalating agents of this invention cannot intercalate into double-strands not comprising the target polynucleotide, and thus, even though the polynucleotide drug is uniformly distributed throughout the body, it will not exert a toxic effect except at its target site.

The property that is changed need not be detectable, although this could be an advantage at times. However, the property changed must enhance the stability of the hybrid comprising the polynucleotide drug/target polynucleotide as compared to a hybrid not comprising the polynucleotide drug.

Methods for preparing a polynucleotide drug comprising an intercalating agent have been described hereinabove in the discussion of the preparation of the polynucleotide probe. These polynucleotide drugs can be administered to a human in an aqueous, neutral solution.

The polynucleotide drug must be delivered to the cell by a suitable carrier. The carrier must prevent the polynucleotide drug from being degraded before it enters the cell, and at the same time must allow the polynucleotide drug to diffuse or to be transported through the cell membrane. One preferred method comprises the use of liposomes.

Liposomes are unilamellar or multilamellar lipid vesicles which enclose a three-dimensional space. The membranes of liposomes are formed by a bimolecular layer of one or more lipid components having polar heads and non-polar tails. In an aqueous (or polar) solution, the polar heads of one layer orient outwardly to extend into the aqueous, or polar, solution and to form a continuous, outer surface. Unilamellar liposomes have one such bimolecular layer, whereas multilamellar vesicles generally have a plurality of substantially concentric bimolecular layers arranged rather like an onion.

Liposomes are well recognized as useful for encapsulating therapeutic agents, such as cytotoxic drugs or other macromolecules capable of modifying cell behaviour, and carrying these agents to in vivo sites. For example, U.S. Pat. No. 3,993,754, by Rahman et al., issued Nov. 23, 1976, discloses an improved method of chemotherapy of malignant tumors, in which an antitumor drug is encapsulated within liposomes and the liposomes are injected into an animal or man. U.S. Pat. No. 4,263,428, by Apple, et al., issued Apr. 21, 1981, discloses an antitumor drug which may be more effectively delivered to selective cell sites in a mammalian organism by incorporating the drug within uniformly sized liposomes. Drug administration via liposomes permits reduced toxicity, altered tissue distribution, increased drug effectiveness, and an improved therapeutic index.

A particularly useful method for encapsulating nucleic acids is disclosed U.S. Pat. No. 4,515,736 by David W. Deamer, issued May 7, 1985, which is hereby incorporated by reference. The method involves novel encapsulation in which liposome dispersions are dried in the presence of a material to be encapsulated. As drying occurs, the individual liposomes fuse to form multilamellar structures which capture the material between lipid lamellae. Upon rehydration, lipid vesicles form which efficiently encapsulate the material. The patent discloses the effective encapsulation of various polynucleotides.

The effectiveness of the polynucleotide drug in displacing an homologous polynucleotide from a target polynucleotide will depend on the length of the polynucleotide portion of the polynucleotide drug and on the number of intercalating agents attached to the polynucleotide drug. The higher the number of intercalating agents, the more effective the polynucleotide portion of the drug will be in a displacing its homologous sequence and the less amount of drug required to prevent transcription or translation of the target polynucleotide. Also, the higher the number of intercalating agents, the faster the drug will bind to the target.

The following examples are by way of demonstration and not by way of limitation.

EXAMPLE I

Preparation of 3-Nitrobenzidine

The procedure followed was basically that of M. S. Lesslie and E. E. Turner, J.C.S., (1934); pp. 1588-92.

To 468 ml 95% sulfuric acid, 87 grams of $P_2O_5$ were added in portions over a period of 2 hours until all the $P_2O_5$ was dissolved ($P_2O_5$ was added to absorb the water in the sulfuric acid). After the solution had cooled to room temperature, 50 grams of benzidine (Fluka Chemical Corp., 255 Oser Avenue, Hauppauge, N.Y. 11788) were slowly added and the temperature was cooled and maintained between 10-15° C.

Finely ground potassium nitrate (50.5 g) was added to the solution under vigorous stirring over a 30 minute period, while the same temperature was maintained. After 60 minutes, the solution was carefully poured into 1500 ml water and this aqueous solution was diluted with boiling water to a total of 6 liters. A 10 ml aliquot was removed and slowly cooled to obtain some 3-nitrobenzidine sulfate crystals. These crystals were used to seed the remaining solution, which was rapidly cooled to 35° C. The solution was further cooled to 20° C. to allow complete precipitation of the 3-benzidine. Following the completion of crystallization, the 3-nitrobenzidine sulfate was filtered off and collected. Thirty gram portions of the moist salt were ground to a stiff paste with water. Concentrated aqueous ammonia was added to the paste, and it was ground further to convert the 3-nitrobenzidine sulfate to free 3-nitrobenzidine. The compound was then collected by dissolving it in a dilute ammonia-ethanol solution and pouring the solution into a large volume of water. The 3-nitrobenzidine precipitated out of the solution. The 46 grams of 3-nitrobenzidine obtained corresponded to a yield of 80.4%.

Preparation of N,N'-biscarbethoxy-3-nitrobenzidine

Twenty nine grams 3-nitrobenzidine were dissolved in 330 ml ethanol containing 39 ml (36 grams) dimethyaniline. Thirty one grams ethylchloroformate were added to the ethanol solution in portions. The solution was then refluxed for 10 minutes after which water was added to precipitate the diurethane derivative. Forty one grams were obtained corresponding to a yield of 95%.

Preparation of 3,8-biscarbethoxy-3-aminobenzidine

Forty one grams of the diurethane were added to a solution containing 500 ml ethanol and 40 ml glacial acetic acid, and the mixture was heated to dissolve the diurethane. The solution was dark brown. The temperature was brought to about 30° C., and zinc powder was gradually added to reduce the nitro groups. The end of the reaction was indicated by the disappearance of the brown color. The zinc was filtered off, and the ethanol and acetic acid were removed under vacuum. The 3,8-biscarbethoxy-3-aminobenzidine was used for the next step without any further purification.

Preparation of
3,8-biscarbethoxy-6-phenylphenanthridine

The procedure followed was adapted from L. P. Wall, J.C.S., (1947), pp. 67-74.

The 3,8-biscarbethoxy-3-aminobenzidine was dissolved in 100 ml nitrobenzene and the solution was heated to a temperature of 150° C. Ten ml benzoyl chloride were added and the temperature maintained at 150° C. until the HCl evolution ceased. After an additional 30 minutes at 150° C., the solution was cooled, and following the addition of ethanol the benzoyl derivative crystallized as colorless prisms. The yield was 35 grams corresponding to 72%.

The benzoyl derivative was dissolved in 70 ml phosphorous oxychloride and refluxed for 1 hour until the evolution of HCl gas had ceased. The yellow solution was cooled to room temperature and then slowly added to a cold dilute ammonia solution to precipitate the phenanthridine. The precipitate was filtered off and dissolved in 200 ml absolute ethanol. Ammonia was then added to discharge the orange color. The compound was precipitated out of solution by the addition of water. The yield was 21 grams corresponding to 62.5%.

Preparation of 5-(4'-bromobutyl)-3,8
biscarbethoxy-6-phenylphenanthridine

This compound was prepared by modifying the procedure of T. T. Watkins, J.C.S., (1952), pp. 3059-3064.

One gram of the 3,8-biscarbethoxy-6-phenylphenanthridine was added to 10 ml of 1,4-dibromobutane that had been preheated to 100° C., so that any water in the mixed solution would evaporate off. The temperature was gradually raised to 150° C. After 30 minutes at 150° C., a yellow precipitate began to form. The mixture was then cooled to room temperature, and ether was added to a total volume of 100 ml to enhance the precipitation. The precipitate was filtered off, washed with ether, and air dried. A total of 0.8 grams of compound was obtained corresponding to a yield of 58%.

The duration of the heating at 150° was important because in a parallel experiment where the mixture was kept at 150° C. for overnight, the resulting product appeared very inhomogeneous and showed very little fluorescence with double-stranded DNA after hydrolysis of the urethane with sulfuric acid. (See the Watkins article on page 3061). This indicated that the compound had decomposed.

Preparation of
5-(4'-bromobutyl)-3,8-diamino-6-phenyl
phenanthridine

Hydrolysis of the urethane moieties were carried out according to the procedure of L. P. Wall, J.C.S., (1947) pp. 67-74.

Eight hundred mg of the 3,8-biscarbethoxy-3-aminobenzidine were dissolved in 10 ml concentrated $H_2SO_4$ under argon gas. After the HBr evolution ceased, five ml $H_2O$ was added and the bath temperature raised to 150° C. The solution was maintained at this temperature for 15 minutes until all the evolution of the $CO_2$ gas had ceased. The mixture was then cooled to 5-10° C., and cold $H_2O$ was added to give a total volume of 150 ml. The solution was neutralized with cold dilute ammonia. Solid potassium bromide to give 1M was added to the solution (to salt out the product), and the solution was permitted to remain at 4° C. overnight. After this period, a precipitate formed which had a permanganate-like crystalline appearance. It was found that the product could also be readily precipitated out of the solution as the ammonium sulfate salt. This product was soluble in water and when mixed with a solution containing double-stranded DNA, resulted in the formation of a strongly fluorescent solution. The 547 mg obtained corresponded to a yield of 89%.

Preparation of 5-(4'-thiobutyl)-3,8-diamino-6-phenylphenanthridine

Sixty mg of 5-(4'-bromobutyl)-3,8-diamino-6-phenyl phenanthridine were dissolved in 4 ml 50% ethanol. One ml of 0.2M $Na_2S_2O_3$ in 50% ethanol was added and the solution heated for 3 hours at 80° C. The ethanol was evaporated with bubbling argon gas at 70° C. and the product precipitated with 2 ml 3M KCl. The precipitate was collected by centrifugation and dissolved in 1 ml 36% HCl. Water (0.35 ml) was added to lower the HCl concentration to 25% and the solution was left at room temperature for 20 hours. A precipitate had formed after this time. Six ml of absolute ethanol were added and the mixture was left at −20° C. for an additional 20 hours to enhance the precipitation. The precipitate was collected by centrifugation, suspended in 1 ml $H_2O$ and the water removed by lyophilization. The yield was 42.5 mg corresponding to 70%. Crude thin layer chromatography showed the presence of 3 fluorescent products. The desired product was not purified before use for the next reaction.

Preparation of Aminodextrans 1.07 grams of dextran T-500 (Pharmacia Biochemicals, Piscataway, N.J.), was added to 15.0 ml of 1M KOH. Three hundred ul butadiene monoepoxide (about 3 mmol) and 30 mg sodium borohydride (catalyst) were then added and the mixture was stirred overnight. The solution was neutralized with HCl, and the excess unreacted butadiene monoepoxide and the dialcohol generated therefrom were extracted four times from the solution with 20 ml ether. The ether remaining in the aqueous solution was evaporated off by bubbling argon gas through the solution. The solution was then dialyzed against 0.2 M sodium acetate, pH 5.0 to remove the salts.

N-bromosuccinimide, 0.5 grams, were then added to the solution and the resulting suspension stirred for 3 hours at 10° C. in the dark. The solution was dialyzed three times against 1 liter of water over a two day period. Two hundred ul of 1M $K_2HCO_3$ and 100 mg cysteamine were added to 0.4 ml of the dialyzate, the mixture was heated under argon at 80° C. for 2 hours, and the solution was desalted by G-50 filtration. The purified dextran contained one derivatized sugar per 20 sugar moieties.

Preparation of Bromoacetylated Aminodextrans

A 0.5 ml solution containing 0.02M sodium borate and eight and one-half mg aminodextran, was mixed with 0.2 ml dimethylformamide and 25 ul of 1M bromoacetic acid N-hydroxy succinimide ester in DMSO. The reaction was followed by measuring the amino content with picrylsulfonic acid (this reagent gives an orange color with primary amino groups). It was found that the reaction was complete after 5 minutes at room temperature. Fifty ul of 1.0M HCl were added to the mixture and the excess of unreacted ester and the generated bromoacetic acid were extracted 4× with water-saturated 1-butanol.

The bromoacetylated dextrans are not very stable, especially at a basic pH. For example, at pH 9.2 and 37° C., all the bromoacetyl groups were cleaved after six hours. Thus, the next reaction should be carried out as soon as possible following isolation of the bromoacetylated dextran.

Preparation of Phenanthridine-Labeled Dextran

Two and one-half mg bromoacetylated dextran were dissolved in 200 ul of aqueous 0.3M sodium acetate, and then mixed with 3.5 mg 5-(4'-thiobutyl)-3,8-diamino-6-phenylphenanthridine in 6 ml formamide. The reaction mixture was allowed to remain for 1 hour at room temperature and then for 1 hour at 37° C. One ml 2M NaCl was added and the unreacted 5-(4'-thiobutyl)-3,8-diamino-6-phenylphenanthridine was extracted 6× with water-saturated 1-butanol. The addition of double-stranded DNA to an aliquot of the aqueous phase resulted in a strong fluorescence indicating that the dextran was labeled with phenanthridine, and that the phenanthridine moieties on the dextran were accessible for intercalation.

Preparation of Poly(dT).Poly(AAdU)

Solution A was prepared containing: 2500 ul 0.25M cacodylate buffer pH 7.2, 250 ul BSA (DNAase free, 20 ug/ml), 50 ul 0.1M $CoCl_2$, and 75 ul 3M NaCl. Solution B was prepared containing 1500 ul $H_2O$ and 50 ul of 0.1M B mercaptoethanol.

Solution A was mixed with Solution B, and 800 units of terminal transferase enzyme, 5 umoles of $^3H$ TTP (low specific activity), and 1.5 umoles AAdUTP were added to the mixed solution. The solution was incubated at 37° C. for 40 hours under argon. During the course of the reaction, cobalt pyrophosphate precipitated from the solution. After 40 hours, the reaction was stopped by the addition of 100 ul 0.5M EDTA. Incubation at 37° C. was continued, however, for 2 more hours to allow the EDTA to complex to and remove the cobaltions that had become complexed to the allylamino groups.

A DEAE cellulose column of 0.6 ml bed volume in a siliconated pasteur pipette was washed twice with 2 ml 1M KOH and then with water until alkaline free. The column was then washed with 2 ml 3M NaCl, followed by 3 ml $H_2O$, and 2 ml 0.2M NaCl. The incubation mixture was then loaded onto the column, and the column was washed sequentially with 2 ml of 0.2M NaCl and 3 ml 0.3M NaCl. The last eluate of the 0.3M wash contained a few percent of the total counts.

The copolymer was eluted off the column with a solution containing 1.5M LiCl in 0.2M acetic acid. Two-tenths ml fractions, were collected. The results are shown below:

| Fractions | Counts per min. (2 ul aliquots); |
|---|---|
| 1 | 40 |
| 2 | 86 |
| 3 | 34516 |
| 4 | 6124 |
| 5 | 1858 |
| 6 | 953 |

Fractions 3-5 were pooled to give a volume of 0.6 ml. Ten ul of this solution was diluted to a volume of 1 ml. The $A_{260}$ of this 1 ml was 0.645 and the $A_{290}$ was 0.203. The absorbance at 290 nm indicated the presence of the allylamino groups. The total $A_{260}$ was 38.7 corresponding to about 1.5 mg of the copolymer.

The ratio of 1:10 of the AAdU to dT was determined by reacting the copolymer with picrylsulfonic acid. Displacement of the sulfonic group by the amino group of the allylamine imparted a yellow color to the copolymer. The measurement of the solution at 420 nm indicated that the ratio of AAdU to dU was 1:10. (It was assumed that every allylamine reacted with a picrylsulfonic acid molecule).

Preparation of Polynucleotide-Labeled Phenanthridine

A solution containing 200 ug of the poly (dT). poly(AAdU) copolymer in 100 ul of 1.5M LiCl and 0.2M acetic acid was brought to about pH 8.0 with 3M $K_2CO_3$. Three mg of the thioalkylated phenanthridine that had been dissolved in 0.6 ml formamide were then added. The mixture was left in the dark for about 90 minutes at room temperature and for an additional 45 minutes at 37° C. One ml $H_2O$ was added and the excess thioalkylated phenanthridine removed by extraction with 1-butanol until the volume of the aqueous phase was reduced to about 300 ul. Additional extractions were then carried out with 1-butanol saturated with water. After each extraction, the two phases were separated by centrifugation. A precipitate appeared after the first 1-butanol extraction. The precipitate contained the labeled polynucleotide and some insoluble phenanthridine side-product. After the last extraction, the material was centrifuged, and the pellet was dissolved in formamide at a temperature of 37° C.

The solution was loaded onto a DEAE cellulose column (chloride form) equilibrated with formamide. The column was washed with formamide to elute the phenanthridine compounds. The phenanthridine-labeled polynucleotide was eluted with 1.1M LiCl in 75:25 formamide:water. For reasons not entirely clear some of the phenanthridine-labeled polynucleotide did not elute off the column even at the higher salt concentration. (To increase the yield, the polynucleotide could be collected by precipitating it with barium acetate in ethanol, collecting the precipitate by centrifugation and dissolving the precipitate in EDTA/$H_2O$. The EDTA complexes the barium and facilitates solution of the precipitate.)

Detection of Fluorescence

Twenty-five ul of the DEAE eluate containing the phenanthridine-labeled polynucleotide were added to (1) a tube containing 10 ug poly(rA) in 0.6 ml 0.1M NaCl, (2) to a tube containing 250 ug calf thymus DNA in 0.6 ml 0.1M NaCl, and (3) to a tube containing poly(dT) in 0.6 ml 0.1M NaCl. The tube with the poly(rA) fluoresced strongly while the other two tubes showed only very weak fluorescence.

The results of this experiment show that this phenanthridine-labeled polynucleotide can be used as a probe in a one step hybridization assay, because this phenanthridine, when attached as described above to a polynucleotide, does not intercalate into other intact double-stranded polynucleotides. It only intercalates into double-stranded polynucleotides formed as a result of the hybridization of the polynucleotide portion of the phenanthridine-labeled polynucleotide with a complementary polynucleotide.

Displacement of a Polynucleotide from Double-Stranded DNA with a Phenanthridine-Labeled Polynucleotide A solution containing poly(dT)-poly(rA) with a ratio of poly(dT) to poly(rA) of 2:1 was mixed with the phenanthridine-labeled poly(dT)-poly(AAdU) at room temperature. The solution began to fluoresce also immediately and the intensity of this fluorescence increased with time. Since the phenanthridine of the phenathridine-labeled poly(dT)-poly(AAdU) does not intercalate into double-stranded calf thymus DNA (see results above), the generation of fluorescence showed that the phenanthridine-labeled polynucleotide had displaced its homologous polynucleotide in the double-stranded hybrid.

It will be apparent to those skilled in the art, that various changes, modifications, and variations can be made without departing from the spirit and scope of the invention as defined by the present claims.

We claim:

1. A single stranded polynucleotide comprising at least two intercalating entities which upon hybridization to a complementary target polynucleotide are capable of generating a detectable change in fluorescence emission of said entities, wherein each of said entities have the structure:

said entities being covalently attached through linker arms to nucleotides in said polynucleotide through the S of the entities, wherein said entities are separated from each other by at least about 10 other nucleotide moieties.

2. The polynucleotide of claim 1, wherein said entities are covalently attached to said nucleotides through an allylamine linker arm to the 5' position of uracil nucleotides in said single stranded polynucleotide and said entities are separated from each other by about a stretch of 10 other nucleotides.

3. The polynucleotide of claim 1, wherein said entities are separated from each other by about a stretch of 10 other nucleotides.

4. The polynucleotide of claim 1, wherein said linker arms are allylamine linker arms.

5. The polynucleotide of claim 1, wherein said linker arms are attached to the base moiety of the nucleotides.

* * * * *